United States Patent
Bruls et al.

(10) Patent No.: US 8,486,689 B2
(45) Date of Patent: *Jul. 16, 2013

(54) MICROELECTRONIC SENSOR DEVICE FOR THE DETECTION OF TARGET PARTICLES

(75) Inventors: Dominique Maria Bruls, Eindhoven (NL); Johannes Joseph Hubertina Barbara Schleipen, Eindhoven (NL); Josephus Arnoldus Henricus Maria Kahlman, Tilburg (NL); Menno Willem Jose Prins, Rosmalen (NL)

(73) Assignee: Koninklijke Philips N.V., Eindhoven (NL)

( * ) Notice: Subject to any disclaimer, the term of this patent is extended or adjusted under 35 U.S.C. 154(b) by 139 days.

This patent is subject to a terminal disclaimer.

(21) Appl. No.: 12/747,529

(22) PCT Filed: Oct. 31, 2008

(86) PCT No.: PCT/IB2008/054541
§ 371 (c)(1),
(2), (4) Date: Jun. 11, 2010

(87) PCT Pub. No.: WO2009/083814
PCT Pub. Date: Jul. 9, 2009

(65) Prior Publication Data
US 2010/0267165 A1  Oct. 21, 2010

(30) Foreign Application Priority Data
Dec. 20, 2007 (EP) .................................. 07123741

(51) Int. Cl.
*C12M 1/00* (2006.01)
(52) U.S. Cl.
USPC ....................................................... 435/283.1
(58) Field of Classification Search
None
See application file for complete search history.

(56) References Cited

U.S. PATENT DOCUMENTS

| 5,532,128 | A | 7/1996 | Eggers et al. |
| 2002/0022276 | A1 | 2/2002 | Zhou et al. |
| 2003/0013185 | A1 | 1/2003 | Saraf |
| 2003/0015428 | A1 | 1/2003 | Becker et al. |
| 2005/0048599 | A1 | 3/2005 | Goldberg et al. |
| 2007/0023643 | A1* | 2/2007 | Nolte et al. ................... 250/288 |
| 2010/0259254 | A1* | 10/2010 | Verschuren et al. .......... 324/244 |

FOREIGN PATENT DOCUMENTS

| WO | 9316383 A1 | 8/1993 |
| WO | 03023363 A2 | 3/2003 |
| WO | 2006134569 A2 | 12/2006 |
| WO | WO 2006/134569 | * 12/2006 |
| WO | 2007136542 A1 | 11/2007 |
| WO | WO 2007/136542 | * 11/2007 |
| WO | WO 2007136542 A1 | * 11/2007 |

OTHER PUBLICATIONS

Lee et al: "Manipulation of Biological Cells Using a Microelectromagnetic Matrix"; Applied Physics Letters, vol. 85, No. 6, Aug. 2004, pp. 1063-1065.

* cited by examiner

*Primary Examiner* — N. C. Yang
*Assistant Examiner* — Richard Moerschell

(57) ABSTRACT

The invention relates to a microelectronic sensor device for the examination of target particles (1) that are bound to binding sites (3) at the binding surface (12) of a carrier (11). In a preferred embodiment, an input light beam (L1) is transmitted into the carrier (11), where a frustrated total internal reflection (FTIR) takes place at the binding surface (12). The amount of light in a resulting output light beam (L2) is detected by a light detector (31) and provides information about the presence of target particles at the binding surface. Moreover, an actuation unit (50) induces movements of the bound target particles (1) by an interaction with a magnetic field (B) or an electric field, particularly with a given modulation frequency (COIn), such that by a demodulation of the detector signal (S) effects of the target particles can be distinguished from background.

11 Claims, 2 Drawing Sheets

MICROELECTRONIC SENSOR DEVICE FOR THE DETECTION OF TARGET PARTICLES

Figure 1:
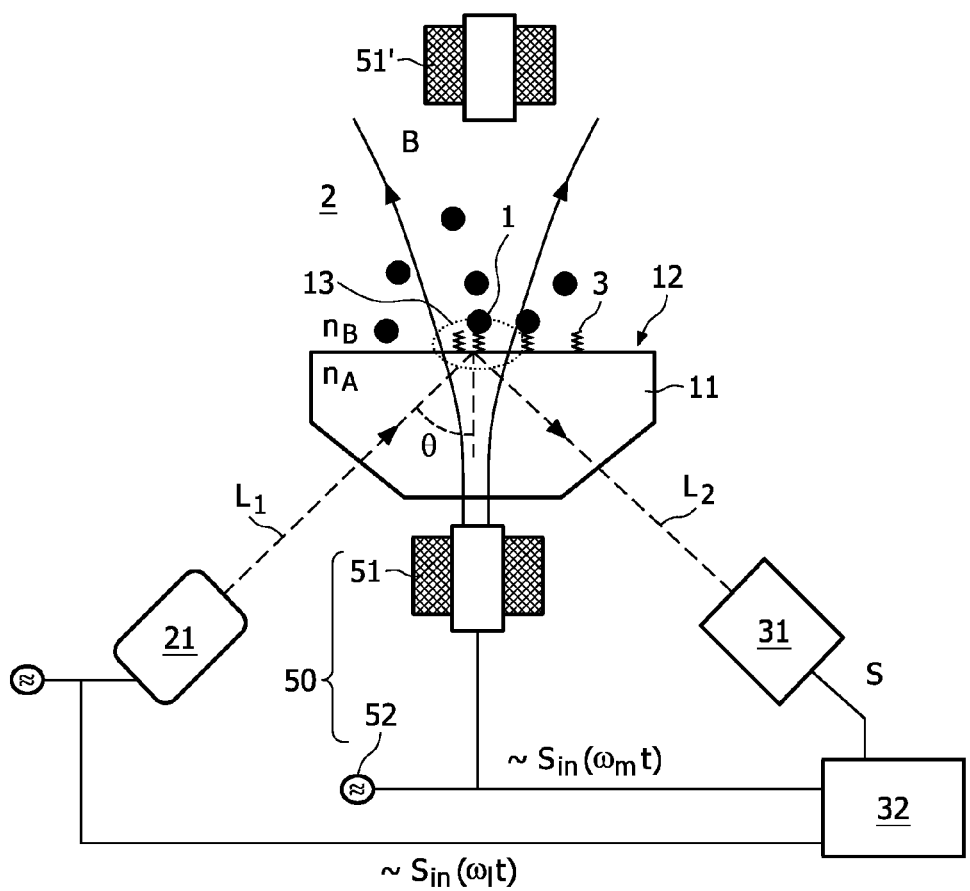

The invention relates to a microelectronic sensor device and a method for the detection of target particles that are bound to binding sites at the binding surface of a carrier. Moreover, it relates to the use of such a device.

The US 2005/0048599 A1 discloses a method for the investigation of microorganisms that are tagged with particles such that a (e.g. magnetic) force can be exerted on them. In one embodiment of this method, a light beam is directed through a transparent material to a surface where it is totally internally reflected. Light of this beam that leaves the transparent material as an evanescent wave is scattered by microorganisms and/or other components at the surface and then detected by a photodetector or used to illuminate the microorganisms for visual observation. A problem of this and similar measurement approaches is that the signal one is interested in is often only a small variation of a large base signal, making accurate and robust measurements difficult, e.g. due to limitations in electronic gain that can be applied on the total signal.

Based on this situation it was an object of the present invention to provide means for an improved detection of bound target particles, wherein it is desired that a higher sensitivity and/or accuracy is achieved.

The microelectronic sensor device according to the present invention serves for the qualitative or quantitative detection of target particles that are bound to binding sites at the "binding surface" of a carrier, wherein said binding surface and carrier (and of course the target particles) do not necessarily belong to the device. The "target particles" may particularly comprise a combination of target components (e.g. biological substances like biomolecules, complexes, cell fractions or cells) and "label particles" (e.g. atoms, molecules, complexes, nanoparticles, microparticles etc.) that have some property (e.g. optical density, magnetic susceptibility, electric charge, fluorescence, or radioactivity) which can be detected. The term nanoparticle is used for particles having at least one dimension ranging between 3 nm and 5000 nm, preferably between 10 nm and 3000 nm, more preferred between 50 nm and 1000 nm. The carrier is usually a solid body, for example from a transparent material like glass or a transparent plastic, having one dedicated surface region that is called "binding surface" here and that comprises at least one, typically however a large number of binding sites. The binding sites will usually be realized by capture molecules that are attached to the binding surface and that can specifically bind to target particles (molecules) in a sample fluid. In general, the binding can be based on a chemical binding, an electrostatic attraction, Van-der-Waals forces or the like.

The microelectronic sensor device comprises the following components:
  a) A sensor unit for providing a "sensor signal" that is indicative of the presence of target particles in an associated sensitive region of the sensor unit. The "sensitive region" is by definition the volume in which the sensor unit can detect target particles. The sensor unit may apply any suitable measurement principle, for example an optical detection, the detection of magnetic or electric fields or susceptibility to these fields, ultrasonic detection or the like.
  b) An "actuation unit" for selectively inducing a movement of bound target particles at the binding surface with respect to the sensitive region of the sensor unit. In this context, a "movement with respect to the sensitive region" shall be a movement within the sensitive region and/or a movement that crosses the border of the sensitive region. In general, the actuation unit may apply any suited effect to achieve the desired movement of target particles, for example mechanical vibrations or a hydrodynamic movement of the surrounding sample fluid or vibrations of the target particles induced by externally applied magnetic and/or electrostatic forces. The movement should be such that the binding of the target particles is preserved and not broken. Typically, the movement will be oscillatory.
  c) An "evaluation module" for evaluating the sensor signal of the sensor unit, wherein this evaluation takes into account the movement of the bound target particles that was induced by the actuation unit. To this end, the induced movement may be detected by a separate measurement, or, preferably, be inferred from a control input of the actuation unit. The evaluation module is therefore typically coupled to both the sensor unit and the actuation unit. It may be realized by dedicated (analog) electronic circuits, digital data processing hardware with associated software, or a mixture of both.

The described microelectronic sensor device has the advantage to allow for a more accurate and robust evaluation of the sensor signals because the measurement of the sensor unit is correlated with the induced movement of the detected target particles. Moving for example all bound target particles out of the sensitive region (or all into the sensitive region) will yield two signals, a measurement with and a reference measurement without target particles, from which the actual effect of the target particles can be inferred with high accuracy.

The invention further relates to a method for the examination of target particles that are bound to binding sites at the binding surface of a carrier, wherein the method comprises the following steps:
  a) Measuring with a sensor unit a sensor signal that is indicative of the presence of target particles in the sensitive region of the sensor unit.
  b) Selectively inducing with an actuation unit a movement of the bound target particles with respect to the sensitive region of the sensor unit.
  c) Evaluating with an evaluation module the sensor signal while taking the induced movement of the target particles into account.

The method comprises in general form the steps that can be executed with a microelectronic sensor device of the kind described above. Therefore, reference is made to the preceding description for more information on the details, advantages and improvements of that method.

In the following, various further developments of the invention will be described that relate both to the microelectronic sensor device and the method defined above.

In a first particular embodiment, the target particles are moved by the activity of the actuation unit through zones of the sensitive region in which the sensor unit has different sensitivity. The target particle will therefore evoke different sensor signals of the sensor unit when being in different sensitivity zones. Preferably, the sensitivity of the sensor unit varies continuously throughout its sensitive region; in this case, even the smallest movement of a target particle induces a variation in the sensor signal of the sensor unit. In general, the non-uniform sensitivity of the sensor unit guarantees that the induced movement of the target particle will have an effect on the sensor signal, which can be taken into account during the evaluation of this signal.

It was already mentioned that the movement of the target particles can be induced in several different ways. In a preferred embodiment, the target particles are moved by an interaction with a magnetic and/or an electric field. This is possible if the target particles have a property to which a magnetic or electric field can couple, e.g. if the particles have a magnetic or electric dipole moment or if such a moment can be induced. In this embodiment the movement of the target particles can very well be controlled by the generation of the magnetic or electric field. For the generation of the field, the actuation unit preferably comprises a field generator, for example a permanent magnet, an electromagnet, or an electrode or electrode pair.

The induced movement of the target particles may optionally be modulated, preferably in a periodical way with a given modulation frequency (wherein the frequency determines the period of some periodic course which needs not necessarily be sinusoidal). To this end, the actuation unit may comprise a modulator for modulating its activity in a controlled and preferably adjustable way. Actively modulating the movement of the bound target particles has the advantage that this movement can be adjusted to a mode that is optimal for the intended evaluation purposes. Moreover, the information about the controlled activity modulation can be exploited by the evaluation module as it implicitly comprises the desired information about the induced movement of the target particles. Thus the control signal with which a modulator controls the actuation unit may in parallel be supplied to the evaluation module for taking it into account during the evaluation of the sensor signal. Furthermore, by inducing and detecting the movement of the particles in the same frequency domain, e.g. by using synchronous modulation and demodulation techniques, noise sources in other frequency domains can be suppressed extremely efficiently.

It was already said that the sensor unit can apply any suitable measurement principle. In a preferred embodiment, the sensor unit applies an optical measurement in which the sensor signal is derived from an output light beam that comes from the carrier and that comprises light from a frustrated total internal reflection of an input light beam at the binding surface. In this embodiment, the microelectronic sensor device will comprise a light source for emitting the input light beam towards the binding surface in such a way—i.e. under an appropriate angle—that it is totally internally reflected there. The light source may for example be a laser or a light emitting diode (LED), optionally provided with some optics for shaping and directing the input light beam. Moreover, the sensor device will comprise a light detector for detecting the mentioned output light beam, wherein this detection typically comprises the measurement of the amount of light in the output light beam (e.g. expressed as the intensity of this beam). The light detector may comprise any suitable sensor or plurality of sensors by which light of a given spectrum can be detected, for example photodiodes, photo resistors, photocells, a CCD chip, or a photo multiplier tube.

For a total internal reflection to occur at the binding surface, this surface must be the interface between two media, e.g. glass and water, at which total internal reflection (TIR) can take place if the incident light beam hits the interface at an appropriate angle (larger than the associated critical angle of TIR). Such a setup is often used to examine small volumes of a sample at the TIR-interface that are reached by exponentially decaying evanescent waves of the totally internally reflected beam. Target particles that are present in this volume can then scatter and/or absorb some of the light of the evanescent waves which will accordingly not be coupled out anymore into the reflected light beam. In this scenario of a "frustrated total internal reflection", the output light beam of the sensor device will comprise the reflected light of the input light beam, wherein the small amount of light missing due to scattering and/or absorption of evanescent waves contains the desired information about the target components in the investigation region. Depending on the concentration of analytes to be measured in the bioassay, the signal one is interested in (missing light) can be very small with respect to a relatively large DC, i.e. constant, background. Furthermore, due to the relatively large background, the signal is prone to disturbances from any source. The proposed application of an induced movement of the target particles helps in this situation to improve the accuracy of the measurements.

According to a further development of the aforementioned embodiment, the input light beam can be modulated, wherein the modulation is preferably done in a periodical way with a given input frequency. Modulating the input light beam provides it with a characteristic fingerprint which allows to distinguish in the sensor signal effects that go back to this input light beam from other effects, e.g. contributions of ambient light.

In the above embodiments in which an output light beam is generated, this beam may optionally be detected with a camera (e.g. a CCD camera) taking exposures with (a) a frequency (frame-rate) that is phase-locked to a modulation frequency $\omega$ of the output light beam but smaller than this modulation frequency $\omega$ (wherein this modulation frequency may for example correspond to a modulated movement of target particles and/or to a modulation of an input light beam);

(b) an exposure time (shutter open) smaller than the modulation period ($T=2\pi/\omega$) of the output light beam.

Thus it is possible to observe with a camera modulation frequencies in the output light beam that are higher than the maximal frame rate of the camera.

The sensor signal that is provided by the sensor unit is preferably demodulated by the evaluation module with respect to one or more given frequencies, particular with respect to a modulation of the induced movement of the target particles and/or with respect to a modulation of an input light beam (if such a modulation and such an input light beam are used). To perform this demodulation, the evaluation unit may comprise a demodulator as it is well known to a person skilled in the art of (analogue or digital) signal processing. With the help of the demodulation, effects that genuinely go back to the target particles and/or the input light beam can be distinguished from other effects, i.e. from disturbances.

In a particular realization of the aforementioned embodiment, the modulation of the induced movement of the target particles and the modulation of an input light beam are adjusted such that the movement-modulation appears in the demodulated sensor signal as a sideband with respect to the light-modulation. This is for example the case if a sinusoidal light-modulation takes place at a much higher frequency than a sinusoidal movement-modulation.

Depending on the particular task the microelectronic sensor device or the method are applied for, the sensor signal may be evaluated with respect to different aspects. Preferably, the sensor signal is evaluated with respect to the presence and/or the amount of target particles in the sensitive region of the sensor unit, thus allowing to determine for example the concentration of particular biomolecules in a sample fluid. Alternatively or additionally, the sensor signal may be evaluated with respect to the binding characteristics of the binding between the target particles and the binding surface. In this case it is exploited that the reaction of the target particles to certain actuation forces, e.g. induced by an electric or magnetic field, depend on the strength with which these target particles are bound, i.e. on the properties of the associated binding sites (capture molecules). Certain aspects of the induced movement of the target particles—like damping factor, resonance frequency, amplitude, phase shift etc.—will therefore carry valuable information about the binding site and/or the operating conditions at the binding surface (e.g. the viscosity of the surrounding fluid).

The invention further relates to the use of the microelectronic device described above for molecular diagnostics, biological sample analysis, or chemical sample analysis, food analysis, and/or forensic analysis. Molecular diagnostics may for example be accomplished with the help of magnetic beads or fluorescent particles that are directly or indirectly attached to target molecules.

Figure 2:
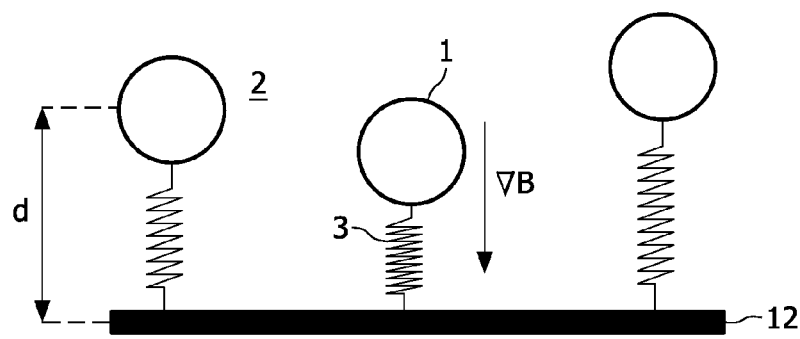

These and other aspects of the invention will be apparent from and elucidated with reference to the embodiment(s) described hereinafter. These embodiments will be described by way of example with the help of the accompanying drawings in which:

FIG. 1 schematically a shows the setup of a microelectronic sensor device according to the present invention;

FIG. 2 shows in more detail target particles that are bound to binding sites at the binding surface of a carrier;

FIGS. 3-6 schematically show several examples of modulation of bound target particles around different axes.

Like reference numbers in the Figures refer to identical or similar components.

FIG. 1 shows a general setup with a microelectronic sensor device according to the present invention. A central component of this setup is the carrier 11 that may for example be made from glass or transparent plastic like polystyrene. The carrier 11 is located next to a sample chamber 2 in which a sample fluid with target components to be detected (e.g. drugs, antibodies, DNA, etc.) can be provided. The sample further comprises magnetic particles, for example superparamagnetic beads, wherein these particles are usually bound (e.g. via a coating with antibodies) as labels to the aforementioned target components. For simplicity only the combination of target components and magnetic particles is shown in the Figure and will be called "target particle 1" in the following. It should be noted that instead of magnetic particles other label particles, for example electrically charged or fluorescent particles, could be used as well.

The interface between the carrier 11 and the sample chamber 2 is formed by a surface called "binding surface" 12. This binding surface 12 is coated with capture elements 3, e.g. antibodies, which can specifically bind to the target particles.

The sensor device comprises a magnetic field generator 51, for example an electromagnet with a coil and a core, for controllably generating a magnetic field B at the binding surface 12 and in the adjacent space of the sample chamber 2. With the help of this magnetic field B, the target particles 1 can be manipulated, i.e. be magnetized and particularly be moved (if magnetic fields with gradients are used). Thus it is for example possible to attract target particles 1 to the binding surface 12 in order to accelerate the binding of the associated target particle to said surface. A second electromagnet 51' at the top of the sample chamber 2 can optionally be used to 'wash' away the particles 1 which have not been bound (e.g. because all binding sites 3 are occupied). This 'washing' can also be accomplished by applying magnetic fields using the first electromagnet 51 in such a way that all unbound target particles are removed from the measurement area/volume, as can be done using a horse-shoe electromagnet configuration. In this case, the binding forces between the target particles 1 and the binding sites 3 should be larger than the applied magnetic forces, therefore the bonds remain intact during the washing procedure (assuming that the bond between the binding sites 3 and the surface 12 is strong enough as well). It should further be noted that also electrostatic forces may be utilized, driving (non-magnetic) label particles using an alternating electric field.

The sensor device further comprises a light source 21, for example a laser or an LED, that generates an input light beam L1 which is transmitted into the carrier 11 through an "entrance window". The input light beam L1 arrives at the binding surface 12 at an angle θ0 larger than the critical angle $\theta_c$ of total internal reflection (TIR) and is therefore totally internally reflected in an "output light beam" L2. The output light beam L2 leaves the carrier 11 through another surface ("exit window") and is detected by a light detector 31. The light detector 31 determines the amount of light of the output light beam L2 (e.g. expressed by the light intensity of this light beam in the whole spectrum or a certain part of the spectrum). The measured sensor signals S are evaluated and optionally monitored over an observation period by an evaluation and recording module 32 that is coupled to the detector 31.

As light source 21, e.g. a commercial CD (λ=780 nm), DVD (λ=658 nm), or BD (λ=405 nm) laser-diode can be used. A collimator lens may be used to make the input light beam L1 parallel, and a pinhole of e.g. 0.5 mm may be used to reduce the beam diameter.

It is possible to use the detector 31 also for the sampling of fluorescence light emitted by fluorescent particles 1 which were stimulated by the evanescent wave of the input light beam L1, wherein this fluorescence may for example spectrally be discriminated from reflected light L2. Though the following description concentrates on the measurement of reflected light, the principles discussed here can mutatis mutandis be applied to the detection of fluorescence, too.

The described microelectronic sensor device applies optical means for the detection of target particles 1. For eliminating or at least minimizing the influence of background (e.g. of the sample fluid, such as saliva, blood, etc.), the detection technique should be surface-specific. As indicated above, this is achieved by using the principle of frustrated total internal reflection. This principle is based on the fact that an evanescent wave penetrates (exponentially dropping in intensity) into the sample 2 when the incident light beam L1 is totally internally reflected. If this evanescent wave then interacts with another medium like the bound target particles 1, part of the input light will be coupled into the sample fluid (this is called "frustrated total internal reflection"), and the reflected intensity will be reduced (while the reflected intensity will be 100% for a clean interface and no interaction). Depending on the amount of disturbance, i.e. the amount of target particles on or very near (within about 200 nm) to the TIR surface (not in the rest of the sample chamber 2), the reflected intensity will drop accordingly. It should be noted that this "near region" is defined by the penetration depth ζ of the evanescent wave in the sample chamber, which depends on wavelength λ, entrance angle θ of the input light beam L1, and on the refractive indices $n_A$ of the substrate 11 and $n_B$ of the medium directly above the interface 12 (e.g. blood or water) and is given by the following formula:

$$\zeta = \frac{\lambda}{2\pi\sqrt{n_A^2 \sin^2\theta - n_B^2}}$$

This intensity drop is a direct measure for the amount of bound target particles 1, and therefore for the concentration of target particles in the sample. When the typical interaction distance of the evanescent wave of about 100 to 200 nm is compared with the typical dimensions of anti-bodies, target molecules and magnetic beads, it is clear that the influence of the background will be minimal. Larger wavelengths λ will increase the interaction distance, but the influence of the background liquid will still be very small.

The described optical measurement procedure is independent of applied magnetic fields. This allows real-time optical monitoring of preparation, measurement and washing steps. The monitored signals can also be used to control the measurement or the individual process steps.

For the materials of a typical application, medium A of the carrier 11 can be glass and/or some transparent plastic with a typical refractive index of $n_A$=1.52. Medium B in the sample chamber 2 will be water-based and have a refractive index $n_B$ close to 1.3. This corresponds to a critical angle $\theta_c$ of 60°. An angle of incidence of θ=70° is therefore a practical choice to allow fluid media with a somewhat larger refractive index (assuming $n_A$=1.52, $n_B$ is allowed up to a maximum of 1.43). Higher values of $n_B$ would require a larger $n_A$ and/or larger angles of incidence.

Advantages of the described optical read-out combined with magnetic labels for actuation are the following:

Cheap cartridge: The carrier 11 can consist of a relatively simple, injection-molded piece of polymer material.

Large multiplexing possibilities for multi-analyte testing: The binding surface 12 in a disposable cartridge can be optically scanned over a large area. Alternatively, large-area imaging is possible allowing a large detection array. Such an array (located on an optical transparent surface) can be made by e.g. ink jet printing of different binding molecules on the optical surface. The method also enables high-throughput testing in well-plates by using multiple beams and multiple detectors and multiple actuation magnets (either mechanically moved or electro-magnetically actuated).

Actuation and sensing are orthogonal: Magnetic actuation of the target particles (by large magnetic fields and magnetic field gradients) does not influence the sensing process. The optical method therefore allows a continuous monitoring of the signal during actuation. This provides a lot of insights into the assay process and it allows easy kinetic detection methods based on signal slopes.

The system is really surface sensitive due to the exponentially decreasing evanescent field.

Easy interface: No electric interconnect between cartridge and reader is necessary. An optical window and an optical-grade measuring surface are the only requirements to probe the cartridge. A contact-less read-out can therefore be performed.

Low-noise read-out is possible.

A problem of the described measurement approach may arise from the fact that the starting signal, i.e. the sensor signal S when no target particles 1 are attached to the binding surface 12, is high. Binding of target particles to the binding surface will decrease this high signal. Thus, the signal 'x' corresponding to the amount of target particles bound to the binding surface is measured in an (1−x) way, as this is the optical signal S. This has a disadvantage, because one is interested in the signal 'x' which is rather small compared to the measured optical signal (1−x). This may cause so-called "gain-problems", as the starting signal is large with respect to the 'x' signal. Therefore it is difficult to amplify the 'x' signal, as the background signal is amplified as well, which can for example result in "overflow" in amplifiers and ADC's, and an amplification of noise contributions e.g. due to laser intensity fluctuations or detector noise etc. Also, the measured 'x' signal is very sensitive to gain variations because gain variations cannot be distinguished from x-changes. Furthermore, if the background signal changes, e.g. because some light from an external source hits the detector or cartridge, the outcome of the measurement is influenced, which is highly undesirable.

It would therefore be highly desirable from the point of view of circuit design and signal processing to convert the (1−x) measurement into a measurement that only measures 'x', i.e. the amount of target particles 1 bound to the binding surface 12.

The solution to the above issues that is proposed here starts with the bioassay as usual, i.e. injection of magnetic beads and sample with target molecules, binding of magnetic beads and target molecules to "target particles" 1, binding of target particles 1 to binding sites 3, and washing away of non-bound target particles. As a result there is a binding surface 12 with target particles 1 that are attached to the surface via capture elements 3, e.g. the protein BSA-opi. The amount of light that is coupled out of the input light beam L1 is proportional to the amount of target particles 1 bound to the binding surface 12. However, the amount of light coupled out is also dependent on the distance d between the target particles 1 and the binding surface 12, i.e. the amount of 'target particle' present in the evanescent field (sensitive region 13) just above the surface.

This is illustrated in FIG. 2 in more detail. As the capture element 3 (between the binding surface 12 and the target particle 1) is flexible, the target particles 1 can be moved up-and-down by applying an alternating magnetic field with a gradient ∇B and/or an electric field (not shown). This will also change the amount of light that is coupled out, which can be observed as "blinking" of the areas where target particles are bound to the surface. Thus there is a signal one can modulate at a certain frequency $\omega_m$, which enables demodulation at this frequency $\omega_m$ of the sensor signal S, i.e. the change of optical amplitude due to the modulated movement of the target particles 1 can be measured. This change is proportional to the amount of target particles 1 present on the binding surface 12, i.e. one has the desired 'x' measurement, rather than a (1−x) measurement.

Changing the distance d between the binding surface 12 and the target particle 1, while stretching and compressing the protein 3 in between, can be done in several ways:

By applying a modulated magnetic field B (as the target particles 1 are super paramagnetic). However, it is not easy to achieve very high frequencies (i.e. frequencies>10 kHz), as the magnetic coils will tend to dissipate a lot of power and will generate a lot of heat. Nevertheless, frequencies of a few kHz are possible.

By electrophoresis: It is possible to attract the target particles 1 to the binding surface 12 using a static magnetic (gradient-)field, and it is possible to repel the target particles 1 from the binding surface 12 by an electric field. When the electric field is switched off, the target particles are pulled back to the surface again by the magnetic field. By applying a periodic electric field, a periodic up-and-down movement of the target particles 1 can be achieved. Using this manner, higher frequencies can be achieved, as it is much easier to generate an HF electric field than an HF magnetic field. The static magnetic field enables larger oscillation amplitudes, thus a higher signal per bound target particle.

The microelectronic sensor device of FIG. 1 incorporates a concrete embodiment of the above approach, i.e. an actuation unit 50 that is used to induce an oscillatory movement of bound target particles 1. The actuation unit 50 comprises a control and modulation unit 52 and the electromagnets 51 and 51' below and above the sample chamber 2, respectively. The control and modulation unit 52 is coupled to the electromagnets 51, 51' to induce a magnetic gradient-field B inside the sensitive region 13. This magnetic field is modulated according to a modulation signal that is proportional to $\sin(\omega_m t)$, wherein this modulation signal is communicated from the control and modulation unit 52 to the evaluation module 32 such that it can be taken into account there. Alternatively, an actuation unit could be designed with electrodes and counter-electrodes below and above the sample chamber 2, respectively, via which a modulated electrical field could be generated within the sample chamber.

By using the above-mentioned modulation method, the sensor signal S can be appropriately demodulated in the evaluation module 32 to achieve a signal that is directly proportional to the amount of target particles 1 that are bound to the binding surface 12. However, the approach also enables measurement of certain properties of the capture elements 3 (e.g. a protein) between the binding surface and the target particles. Thus structural information on the protein can be derived from the observed Q-factor and resonance frequency, and the size of the protein can be derived from the observed amplitude of the target particle oscillation. Moreover, the viscosity of the fluid (e.g. saliva) in which the measurement takes place can also be inferred.

Furthermore, because of the non-linear relation between the detected signal and the z-position of the particles above the sensor surface, harmonics in the modulated signal gives information about the average of said z-position. This can be used to measure the length of the binding with respect to the optical surface, as well as to characterize the binding probes.

In the described method, the value of 'x' which is derived from the sensor signal S by demodulation is independent of the background signal. Furthermore 'x' cannot be influenced by any disturbances that occur at a different frequency than the frequency used for modulation/demodulation, e.g. external light, electronic interference etc.

Figure 3:
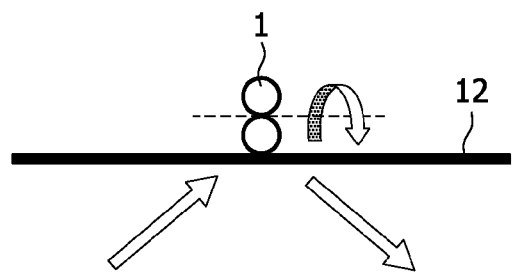

FIG. 3 schematically shows a further example of the invention. Shown is a binding surface 12 similar to the Figs described above. The two arrows below the binding surface 12 indicate the course light impinging at the binding surface 12, as indicated by the left arrow, and being reflected from the binding surface 12, as indicated by the right arrow. The arrowheads symbolize the direction of light to the binding surface 12 and away from the binding surface 12, respectively. In FIG. 3 two target particles 1 are shown bound to each other and bound to the binding surface 12. This cluster of target particles 1 forms a physical figure that is asymmetrical and thereby non uniform forces are exerted to these target particles 1. More generally, individual or combined target particles are used to which a mechanical torque can be applied, which requires a non-spherical physical property of the particles (or of the combination of particles). For example a target particle can have a magnetic and/or electric anisotropy, e.g. a shape anisotropy and/or a crystalline anisotropy. Target particles 1 can be made to be detectable regarding the force and orientation exerted by means of a non-uniform physical and/or chemical property. A physical property may be an electromagnetic property, e.g. an optical property such as an orientation-dependent optical absorption. A chemical property may be a chemical moiety as a coating of the target particles 1. For example the target particle 1 may be non-spherically coated with an optically active moiety, e.g. a chemiluminescent enzyme or substrate. When the chemiluminescent reaction is enabled while the target particle orientation is modulated as described, in an optical field the resulting optical signal will also be modulated. Detecting this modulated signals it is suggested to discriminate between different types of target particles 1, and also it is suggested to discriminate between different types of biological bindings between the target particles 1. This means by exploiting the rotation of the target particles 1 a conclusion can be drawn on the character of the target particles 1 and on the character of the binding of the target particles 1. A further effect of detection of target particles 1 having a rotation as described is the improved sensitivity, by this means detection sensitivity is enhanced. In an example the outcoming light is not completely reflected, but depending on the amount of target particles 1, especially the label particles comprised in the target particles 1, outcoming light at the right side is diminished with regard to the incoming light at the left side. This is due to reflections of light at the label particles which are correlated to the number or amount of target components (e.g. biological substances like biomolecules, complexes, cell fractions or cells).

Figure 4:
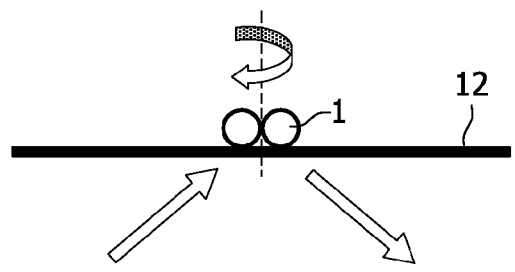
Figure 5:
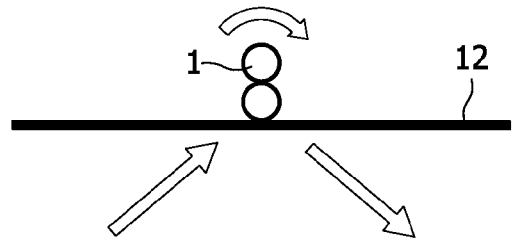

A dashed line shown in FIG. 3 sketches an axis of rotation around which the target particles 1 are rotatable, in this example a cluster of two target particles 1 bound together. To further illustrate the direction of rotation a curved twin arrow is shown which gives the direction of rotation of the target particle 1 out of the image plane. By changing the electric or magnetic field causing the force for rotation the rotation direction can be changed to the contrary direction showing into the image plane. The rotation of the target particles 1 is supposed to be caused by their physical properties, as the form of the two-particle cluster of target particles 1 is not perfectly spherical and consequently a non homogeneous force or torque is exerted to the target particles 1 leading to a rotation. FIG. 4 shows a similar example of the invention, here the target particles 1 are again bound to each other forming a cluster of two and are arranged essentially in the same distance in parallel to the binding surface 12. The rotation axis is shown as a dashed line perpendicular to the binding surface 12. This means the direction of rotation is essentially parallel to the binding surface 12 leading to a rotational movement of the target particles 1 at which the distance of the target particles 1 to the binding surface 12 essentially stays the same. Again, the rotation direction can be changed, in clockwise direction or against clockwise direction. FIG. 5 shows a further example at which the rotation direction lies within the image plane of the Figs, the rotation axis is therefore directed into the image plane of the Figs. As the target particles 1 are bound as a cluster of two, the rotation around this axis means that the target particles change their relative positions in time.

Figure 6:
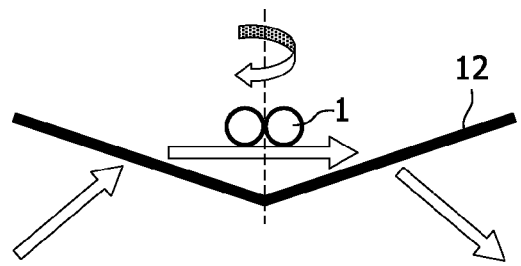

Another structure of the binding surface 12 is shown in FIG. 6 in connection with a different optical detection method. The binding surface 12 is not a flat surface as described in FIG. 3-5 but is a bent surface being symmetric to a vertical axis lying in the image plane. One part of the binding surface 12 is declined, the other part of the binding surface 12 is inclined with both parts having the same length and crossing in the middle, forming a symmetrical sink. As a consequence there is no total reflection of light at the binding surface 12, as is shown in FIG. 3-5, but in FIG. 6 incoming light is mainly directed through one declined part of the binding surface 12 and diffracted in a direction to the opposed other inclined part of the binding surface 12. Before reaching the inclined part of the binding surface 12 the light passes the target particles 1, where light is absorbed. At the inclined part of the binding surface 12 the light passes the binding surface 12 again and is diffracted again in the same direction, as is shown in FIG. 6. A detector receives the reflected light coming from the structure described, see also FIG. 1. The rotation of the target particles 1 in this example is the same as described under FIG. 4, further rotation directions are designable.

A problem of a modulation of the target particle movement with a low frequency $\omega_m$ may be that the detection of the resulting low frequent signals takes place in a range where 1/f noise (electronics) may have a predominant contribution to the demodulated signal noise. To address this issue, an additional intensity modulation of the light source 21 and an associated demodulation technique can be used. FIG. 1 indicates in this respect that also the input light beam L1 emitted by the light source 21 is modulated, and that the corresponding sinusoidal modulation signal $\sin(\omega_1 t)$ is communicated to the evaluation module 32. High frequency modulation (up to several 100 MHz) of a laser diode can be achieved in a straightforward manner just by modulating the injected laser current. This laser current modulation is widely used in optical storage applications for suppressing intensity noise due to optical feedback. By combining this light intensity modulation (high frequency $\omega_1$) with the aforementioned magnetic or electric field modulation (moderate frequency $\omega_m$), the signal due to modulation of the moderate frequency magnetic/electric field (the "oscillating target particle" signal) can be translated to the high frequency domain which is advantageous with respect to electronics noise. The oscillating target particle signal appears in this scheme as a sum and difference sideband in the high frequency (MHz) domain according to the formula:

$$A \cdot \cos(\omega_l t) \times \cos(\omega_m t) = \frac{1}{2} A[\cos(\omega_l - \omega_m)t + \cos(\omega_l + \omega_m)t]$$

By using this double modulation scheme, the (moderate frequency) oscillating target particle signal can be measured conveniently at high frequencies. In order to eliminate erroneous cross-talk from the signal due to laser intensity variations and stray reflections (present at frequency $\omega_1$), the sidebands should be sufficiently separated from the main band occurring at $\omega_1$. This requires a stable oscillation circuitry driving the laser. Using a laser modulation frequency $\omega_1$ of for example 100 kHz and a magnetic or electric field modulation frequency $\omega_m$ of 1 kHz, the stability of the laser driver should be well below 1 kHz when operated at 100 kHz, which can be readily achieved in practice.

Furthermore, because of the non-linear relation between the detected signal and the z-position of the particles above the sensor surface, higher inter-modulation terms in the signal give information about the average of said z-position. This can be used to measure the length of the binding with respect to the optical surface, as well as to characterize the binding probes.

When a (CCD) camera is used to observe the binding surface 12, said camera may be too slow to follow the modulation of a magnetic or electric field (frequency $\omega_m$) and/or of a laser input light beam (frequency $\omega_1$). This problem can be solved by (1) phase-lock the camera frame rate to the modulation frequency and
(2) adjust the illumination (shutter open) time sufficiently short to sample (a part of) the modulation period.

By shifting phase of the illumination moment with respect to the modulation period, the total period can be scanned. Using a camera has advantages in multi-spots processing compared to single-spot approaches.

While the invention was described above with reference to particular embodiments, various modifications and extensions are possible, for example:

The sensor can be any suitable sensor to detect the presence of magnetic particles on or near to a sensor surface, based on any property of the particles, e.g. it can detect via magnetic methods, optical methods (e.g. imaging, fluorescence, chemiluminescence, absorption, scattering, surface plasmon resonance, etc.), sonic detection (e.g. surface acoustic wave, etc), electric detection, etc.

In addition to molecular assays, also larger moieties can be detected with sensor devices according to the invention, e.g. cells, viruses, or fractions of cells or viruses, tissue extract, etc.

The detection can occur with or without scanning of the sensor element with respect to the sensor surface.

Measurement data can be derived as an end-point measurement, as well as by recording signals kinetically or intermittently.

The device and method can be used with several biochemical assay types, e.g. binding/unbinding assay, sandwich assay, competition assay, displacement assay, enzymatic assay, etc.

The device and method are suited for sensor multiplexing (i.e. the parallel use of different sensors and sensor surfaces, e.g. different capture probes can be spotted on the surface, e.g. via spotting or ink jet printing on an optical substrate), label multiplexing (i.e. the parallel use of different types of labels) and chamber multiplexing (i.e. the parallel use of different reaction chambers).

The device and method can be used as rapid, robust, and easy to use point-of-care biosensors for small sample volumes. The reaction chamber can be a disposable item to be used with a compact reader, containing the one or more field generating means and one or more detection means. Also, the device, methods and systems of the present invention can be used in automated high-throughput testing. In this case, the reaction chamber is e.g. a well-plate or cuvette, fitting into an automated instrument.

Finally it is pointed out that in the present application the term "comprising" does not exclude other elements or steps, that "a" or "an" does not exclude a plurality, and that a single processor or other unit may fulfill the functions of several means. The invention resides in each and every novel characteristic feature and each and every combination of characteristic features. Moreover, reference signs in the claims shall not be construed as limiting their scope.

The invention claimed is:

1. A microelectronic sensor device for the examination of target particles that are bound to binding sites at a binding surface of a carrier, the microelectronic sensor device comprising:
   a sensor unit having a sensitive region, wherein the sensor unit comprises:
      a generator configured to generate an input signal, to modulate the input signal at a first modulation frequency, and to provide the modulated input signal to the carrier, and
      a detector configured to receive from the carrier an output signal which is generated in response to the modulated input signal, wherein the output signal is modulated at the first modulation frequency and changes depending upon the presence of target particles in the sensitive region of the sensor unit, and wherein the detector is configured to generate, in response to the output signal, a sensor signal that is indicative of the presence of target particles in a sensitive region of the sensor unit;

an actuation unit configured to selectively induce a movement of the bound target particles with respect to the sensitive region of the sensor unit: and an evaluation module configured to evaluate the sensor signal taking the induced movement of the target particles into account and further taking into account the first modulation frequency.

2. The microelectronic sensor device of claim 1, wherein the actuation unit is configured to move the target particles through zones of different sensitivity in the sensitive region of the sensor unit.

3. The microelectronic sensor device of claim 1, wherein the actuation unit is configured to generate at least one of an electric field and a magnetic field, and wherein the target particles are moved by an interaction with the at least one of the magnetic field and the electric field.

4. The microelectronic sensor device of claim 1, wherein the actuation unit is configured to cause the induced movement of the bound target particles to be periodic, having a second modulation frequency different from the first modulation frequency.

5. The microelectronic sensor device of claim 1, wherein the target particles have non-spherical forms, and wherein the actuation unit causes the induced movement of the bound target particles to be modulated around an axis running through the target particles.

6. The microelectronic sensor device of claim 4, wherein the second modulation frequency produces in the sensor signal sidebands with respect to the first modulation frequency, and wherein the evaluation unit includes a demodulator configured to demodulate the sensor signal.

7. A method of sensing presence of target particles bound to binding sites at a binding surface of a carrier, the method comprising:

employing a signal generator to generate an input signal, to modulate the input signal at a first modulation frequency, and to provide the modulated input signal to the carrier;

at the carrier, generating an output signal in response to the modulated input signal, wherein the output signal is modulated at the first modulation frequency and changes depending upon the presence of target particles in the sensitive region of the sensor unit;

at a detector, receiving from the carrier the output signal and in response to the output signal, producing a sensor signal that is indicative of the presence of target particles in a sensitive region of the sensor unit;

selectively inducing a movement of the bound target particles with respect to the sensitive region of the sensor unit; and evaluating with an evaluation unit the sensor signal, taking the induced movement of the target particles into account and further taking into account the first modulation frequency.

8. The method of claim 7, further comprising the actuation unit moving the target particles through zones of different sensitivity in the sensitive region of the sensor unit.

9. The method of claim 7, further comprising the actuation unit generating at least one of an electric field and a magnetic field, wherein the target particles are moved by an interaction with the at least one of the magnetic field and the electric field.

10. The method of claim 7, further comprising the actuation unit causing the induced movement of the bound target particles to be periodic, having a second modulation frequency different from the first modulation frequency.

11. The method of claim 7, wherein the target particles have non-spherical forms, and further comprising the actuation unit causing the induced movement of the bound target particles to be modulated around an axis running through the target particles.

* * * * *